(12) United States Patent
Azegrouz

(10) Patent No.: US 9,271,644 B2
(45) Date of Patent: Mar. 1, 2016

(54) LASER SCANNING SYSTEMS

(75) Inventor: Hind Azegrouz, Madrid (ES)

(73) Assignee: Optos PLC, Dunfermline (GB)

( * ) Notice: Subject to any disclaimer, the term of this patent is extended or adjusted under 35 U.S.C. 154(b) by 1045 days.

(21) Appl. No.: 13/389,060

(22) PCT Filed: Jul. 29, 2010

(86) PCT No.: PCT/GB2010/051247
§ 371 (c)(1),
(2), (4) Date: Apr. 16, 2012

(87) PCT Pub. No.: WO2011/018644
PCT Pub. Date: Feb. 17, 2011

(65) Prior Publication Data
US 2012/0188614 A1    Jul. 26, 2012

(30) Foreign Application Priority Data
Aug. 10, 2009   (GB) .................................. 0913911.4

(51) Int. Cl.
*A61B 3/00*       (2006.01)
*A61B 3/10*       (2006.01)

(52) U.S. Cl.
CPC .................................... *A61B 3/1025* (2013.01)

(58) Field of Classification Search
USPC ........................ 351/206, 246; 372/20; 358/474
See application file for complete search history.

(56) References Cited

U.S. PATENT DOCUMENTS

| | | |
|---|---|---|
| 5,815,242 A | 9/1998 | Anderson et al. |
| 6,160,826 A | 12/2000 | Swanson et al. |
| 2002/0151774 A1 | 10/2002 | Soller et al. |
| 2003/0103249 A1 | 6/2003 | Hartmann et al. |
| 2007/0291277 A1 | 12/2007 | Everett et al. |

FOREIGN PATENT DOCUMENTS

| | | |
|---|---|---|
| EP | 0024521 A1 | 3/1981 |
| EP | 0698991 A2 | 2/1996 |
| EP | 0730428 A1 | 9/1996 |
| EP | 2040606 | 4/2009 |
| GB | 2440163 A | 1/2008 |
| JP | H03198039 A | 8/1991 |
| JP | H03227168 A | 10/1991 |
| JP | 06-148525 | 5/1994 |
| JP | 09197280 A | 7/1997 |
| JP | 2002098901 A | 4/2002 |
| JP | 2005326220 A | 11/2005 |
| JP | 2010508932 A | 3/2010 |
| WO | WO-92/19930 A1 | 11/1992 |
| WO | WO-95/13012 A2 | 5/1995 |
| WO | WO-2008/009877 A1 | 1/2008 |
| WO | WO-2008/056110 A2 | 5/2008 |
| WO | WO-2009/029604 A2 | 3/2009 |
| WO | WO-2010/125394 A1 | 11/2010 |

OTHER PUBLICATIONS

Alvazzi Delfrate, S., "International Search Report" for PCT/GB2010/051247, as mailed Nov. 17, 2010, 3 pages.

*Primary Examiner* — Jack Dinh
(74) *Attorney, Agent, or Firm* — Winstead PC

(57) ABSTRACT

The invention provides a method of reducing jitter error in a laser scanning system (1) adapted to produce a scanned image comprising a number of lines of an object (18). The method comprising the steps of providing a reference object (22) arranged such that the scanned image produced by the laser scanning system (1) includes a reference image (24) of the reference object (22); processing the reference image (24) to calculate an error arising from non-repeatable displacement of the lines of the reference image (24); and adjusting at least one operating parameter of the laser scanning system (1) in response to the calculated error.

61 Claims, 10 Drawing Sheets

LASER SCANNING SYSTEMS

The present invention relates to laser scanning systems, especially, but not exclusively, to laser scanning systems utilised in scanning laser ophthalmoscopes.

Laser scanning systems, such as those found in scanning laser ophthalmoscopes, typically comprise of a high speed rotating polygonal mirror and a motor driven slow speed mirror which are used to create a raster scan pattern of, for example, a human retina. The polygon mirror has a plurality of facets and provides the vertical scanning of the laser beam, and the slow speed mirror provides the horizontal scanning of the laser beam. Each facet of the polygon mirror generates one vertical scan line of image per polygon rotation.

The resolution of the images produced by such systems relies on an accurate timing of the polygon facet arrival in position which triggers the recording of a scan line.

A conventional approach to ensuring an accurate timing of the polygon facet arrival involves the use of a facet detector. The facet detector uses a laser beam that impacts on the polygon facet from a side angle and detects when the orientation of the facet is normal to the plane of the detector. When the polygon facet is in position an electronic system triggers a clock signal for the recording of a scan line. The timing signal of facet arrival is therefore used for accurate line scan registration.

However, the facet detector and the polygon both introduce some "jitter" error to the scanned image. Jitter is the non-repeatable displacement of a line along the scan direction. The effect of this jitter error is to introduce vertical shifts between vertical lines of the scanned image, which affects the quality of the image produced.

Jitter error can be either random or periodic in nature. Jitter error may result from:
(a) Imperfect timing of the polygon facet position. If the clock signal is started when the polygon facet is not exactly normal to the plane of the detector, the entire vertical line of the image will be shifted in the vertical direction.
(b) Random noise introduced by the electronic triggering system of the facet detector. If the triggering of the clock signal for the recording of a scan line is early, or late, the entire vertical line of the image will be shifted in the vertical direction.
(c) Variations of the cut depth in the facets of the polygon. Facet cut depth error is the deviation from facet to facet of the distance from the centre of the facet to the centre of the axis of rotation. The effect of these variations is to cause periodic vertical shifts in the scan line.
(d) Variations in the flatness of the facet of the polygon. Variations in flatness from facet to facet will result in periodic jitter in the scan line.
(e) Variations in the rotational speed of the polygon. The rotational speed of the polygon can be affected by noise from the mounting bearings. The effect of these variations in rotational speed of the polygon is to cause random vertical shifts in the scan line.

It is an object of the present invention to provide improved techniques for removing jitter error in laser scanning systems.

According to a first aspect of the present invention there is provided a method of reducing jitter error in a laser scanning system adapted to produce a scanned image comprising a number of lines of an object, the method comprising the steps of:
providing a reference object arranged such that the scanned image produced by the laser scanning system includes a reference image of the reference object;
processing the reference image to calculate an error arising from non-repeatable displacement of the lines of the reference image; and
adjusting at least one operating parameter of the laser scanning system in response to the calculated error.

Adjusting the at least one parameter of the laser scanning system in response to the calculated error exploits the linear dependency between the error arising from the non-repeatable displacement of the lines of the reference image and line shifts in the reference image. This allows the line shifts to be incorporated as operating parameter control variables in the laser scanning system to reduce the jitter error when capturing an image.

The reference object may be periodic in the direction of the line of scan of the laser scanning system. The line of scan is the line in which the scanning laser beam moves across the reference object as it produces a line of the scanned image.

The reference object may include a series of alternate black and white bands. The alternate black and white bands may be equally spaced. The width of each band may be between 0.25 mm and 0.75 mm. Preferably, the width of each band is 0.5 mm. The reference image thus contains a plurality of columns of alternate black and white sections.

The reference image may comprise a number of pixels.

The laser scanning system may further comprise a source of collimated light.

The laser scanning system may comprise first and second scanning elements. The first scanning element may be a rotating polygonal mirror. The second scanning element may be an oscillating plane mirror.

The reference object may be positioned in the optical path of the laser scanning system after the first scanning element. That is, the reference object may be positioned in the optical path of the laser scanning system between the first scanning element and the second scanning element.

When the first scanning element is a rotating polygonal mirror and the reference object is positioned after the polygon in the optical path, the scanning laser beam repeatedly moves across the same portion of the reference object to produce the reference image. That is, the reference image is constructed of a plurality of repeat image scans of the same portion of the reference object. The scanned image produced by the laser scanning system in this case includes only this reference image.

The source of collimated light and the first and second scanning elements may combine to provide a two-dimensional collimated light scan.

The second scanning element may be positioned in the optical path of the laser scanning system after the first scanning element and the reference object may be positioned after the second scanning element such that the source of collimated light and the first and second scanning elements combine to produce a two-dimensional raster scan light pattern across the reference object to produce the reference image thereof.

The laser scanning system may further comprise scan transfer means having two foci.

The source of collimated light and the first and second scanning elements may combine to provide a two-dimensional collimated light scan from an apparent point source, and the apparent point source may be provided at a first focus of the scan transfer means and an object may be accommodated at a second focus of the scan transfer means, and wherein the scan transfer means may transfer the two-dimensional collimated light scan from the apparent point source to the object.

The object may be an eye and the scan transfer means transfers the two-dimensional collimated light scan from the apparent point source into the eye.

The scan transfer means may comprise an elliptical mirror. The scan transfer means may comprise an aspherical mirror. The scan transfer means may comprise an ellipsoidal mirror. The scan transfer means may comprise a pair of parabola mirrors. The scan transfer means may comprise a pair of paraboloidal mirrors.

The laser scanning system may further comprise scan relay means. The source of collimated light, the first and second scanning elements and the scan relay means may combine to provide the two-dimensional collimated light scan from the apparent point source.

The scan relay means may comprise two foci. One foci of the scan relay means may be coincident with one foci of the scan transfer means.

The scan relay means may comprise an elliptical mirror. The scan relay means may comprise an aspherical mirror. The scan relay means may comprise an ellipsoidal mirror. The scan relay means may comprise a pair of parabola mirrors. The scan relay means may comprise a pair of paraboloidal mirrors.

The reference object may be located on one of the scan transfer means or scan relay means.

The scanned image produced by the laser scanning system may include an image of the object and the reference image of the reference object.

The image of the object and the reference image of the reference object may occur beside one another on the scanned image.

The reference image may extend along an edge portion of the scanned image.

The step of processing the reference image may include assigning one column of the reference image as the reference column. Preferably, the reference column is located around the centre of the reference image.

The step of processing the reference image may include generating data signals for one or more columns which are representative of the image information of the column. The image information of the column may include the light intensity, or brightness, of the image and the data signals may include values which are representative of this intensity, or brightness. The light intensity, or brightness, may include the light intensity or brightness of each pixel in the reference image. Preferably, data signals are generated for each column of the reference image.

The step of processing the reference image may further include comparing the reference column data signal with one or more data signals from the other columns. Preferably, the reference column data signal is compared with every other column data signal.

The comparison between the reference column data signal and the other column data signals may further include determining the similarities between the signals. Preferably, comparison between the reference column data signal and the other column data signals includes determining the warping between the signals.

The comparison between the reference column data signal and the other column data signals may include using a dynamic time warping algorithm. The comparison between the reference column data signal and the other column data signals may include using a derivative dynamic time warping algorithm.

The comparison between the reference column data signal and the other column data signal may include generating a matrix which is representative of the pair-wise distances between the reference column data signal and the other column data signal. A matrix is generated for each comparison of the reference column data signal with every other column data signal. The distances between each column may be defined in terms of pixels. That is, the distance between corresponding points of each signal may be represented by an integer number of pixels.

The comparison between the reference column data signal and the other column data signal may alternatively include generating a matrix which is representative of the pair-wise distances between the derivative of the reference column data signal and the derivative of the other column data signal. A matrix is generated for each comparison of the reference column data signal with every other column data signal. Preferably, the derivative is the pair-wise distances between the first derivative of the reference column data signal and the derivative of each of the other column data signals.

The comparison between the reference column data signal and the other column data signals further includes determining a function representative of the minimal distance path of the matrix. The minimal distance path may be termed the "alignment path", the "optimal path", the "minimal cost path", the "warping path", or the "warping function".

The determination of the function representative of the minimal distance path of the matrix may include applying one or more constraints. The constraints may include that the function satisfies a boundary condition criteria, where the starting and end points of the function must be the first and last points of the sequence. That is, this requires the function to start and finish in diagonally opposite corners of the matrix. The constraints may further include that the function satisfies the monotonicity criteria. That is, this requires the function to be monotonically spaced in time (i.e. the function must be increasing in time). The constraints may further include that the function satisfies the continuity criteria. This restricts the allowable steps in the warping path to adjacent cells. That is, the function can only progress in steps of one at a time.

The step of processing the reference image may further include determining an approximate signal shift between the reference column data signal and each of the other column data signals. The signal shift may correspond to a column shift in the reference image. The column shift corresponds to the error arising from the quasi-periodic displacement of the columns of the reference image.

The determination of the approximate signal shift between the reference column data signal and the other column data signals may include transforming a parametric representation of the function to an explicit form.

The transformation may include removing duplicates of the abscissas of the parametric curve.

The transformation may include interpolation of the explicit form of the function.

The determination of the approximate signal shift between the reference column data signal and each of the other column data signals may include determining the distance between the interpolated path defined by the explicit function and a reference path in the matrix.

The reference path in the matrix corresponds to the matrix diagonal.

The parametric representation of the matrix diagonal is $X=t$, $Y=t$, $t$ in $[1,N]$, where $N$ is the signal length. The implicit form is $Y=X$. The implicit form corresponds to the path between the two signals if they were identical.

The step of processing the reference image may include determining an average approximate signal shift for all column data signals originating from the same portion of the scanning element of the laser scanning system.

The step of processing the reference image may include determining an average approximate signal shift for all column data signals originating from the same facet of the rotating polygonal mirror.

The step of adjusting the at least one operating parameter of the laser scanning system in response to the calculated error may include adjusting the capture time of the first or second scanning elements.

The capture time is the time taken to record a scan line across the scanning element.

The capture time of the first or second scanning element may be advanced and/or delayed.

Where the first or second scanning element is a rotating polygonal mirror, each facet of the polygon may have a specific capture time.

The capture time for each facet of the polygon may be determined by advancing or delaying a reference capture time by a factor dependent upon the average approximate signal shift for that specific portion of the scanning element. The specific portion of the scanning element may be a facet of the polygon.

According to a second aspect of the present invention there is provided a mirror for a laser scanning system including a reference object.

The reference object may be periodic in the direction of the line of scan of the laser scanning system. The reference object may be made up of a series of alternate black and white bands.

The mirror may be an elliptical mirror, an aspherical mirror, an ellipsoidal mirror, a parabola mirror or a paraboloidal mirror.

Embodiments of the present invention will now be described, by way of example only, with reference to the accompanying drawings, in which.

Figure 1:
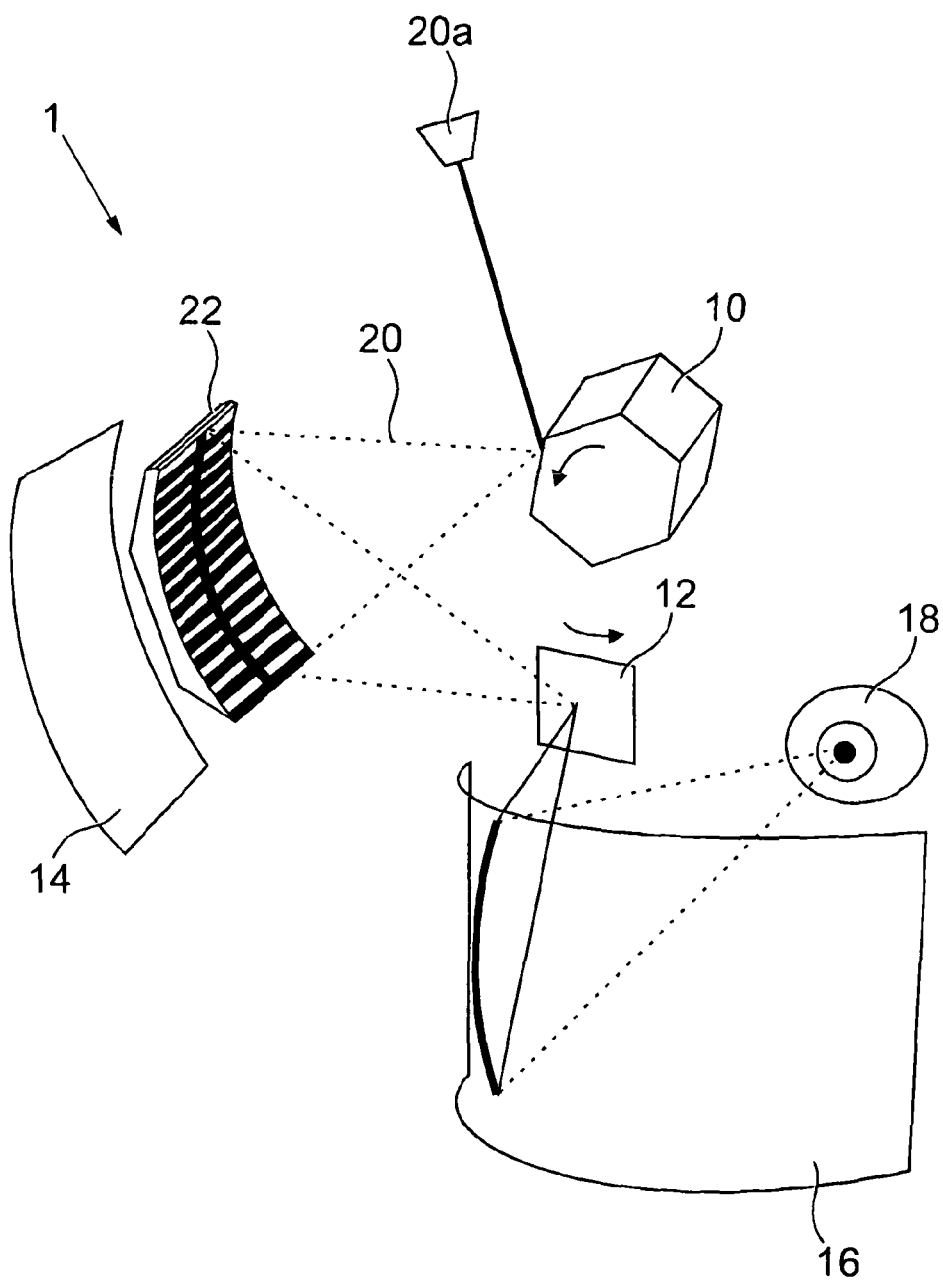
FIG. 1 is a schematic view of the scanning and reflecting elements of a laser scanning ophthalmoscope.

FIG. 1 is a schematic view of the scanning and reflecting elements of the laser scanning system 1, as applied to a scanning laser ophthalmoscope (SLO). As illustrated, the main components are a high speed rotating polygon mirror 10 (an example of a first scanning element), a slow speed mirror 12 (an example of a second scanning element), a first ellipsoidal mirror (slit mirror) 14 (an example of scan relay means) and a second ellipsoidal mirror (main mirror) 16 (an example of a scan transfer means).

The slow speed mirror 12 may be an oscillating plane mirror, such as a galvanometer mirror.

The rotating polygon mirror 10 is located at the first focal point of the slit mirror 14 and the slow speed mirror 12 is located at the second focal point of the slit mirror 14. The slow speed mirror 12 is also located at the first focal point of the main mirror 16. A patient's eye 18 is located at the second focal point of the main mirror 16.

A source of collimated light 20a produces a laser light beam 20. The laser light beam 20 is then reflected from the polygon 10 to the patient's eye 18 via the slit mirror 14, the slow speed mirror 12 and the main mirror 16.

Figure 2:
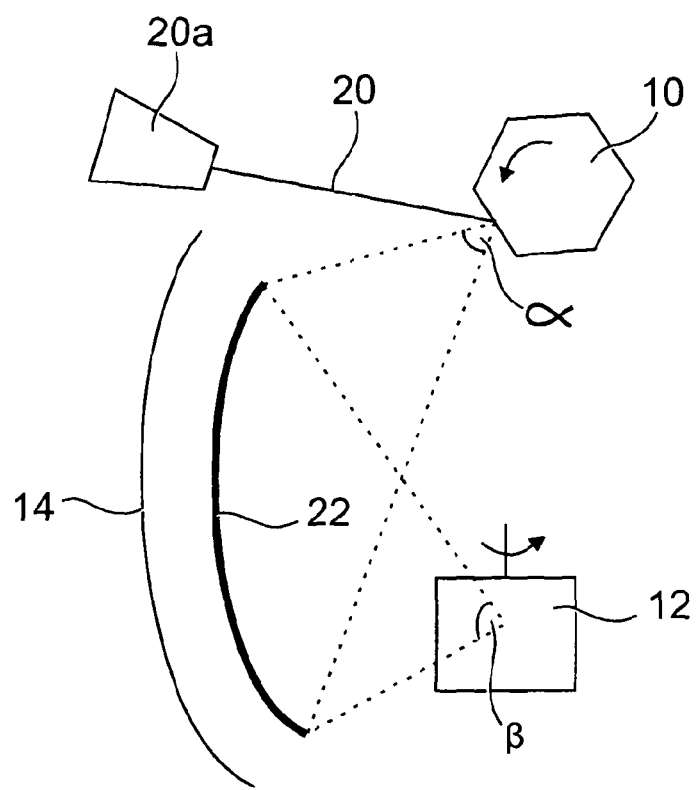
FIG. 2 is a first partial schematic view of the elements of FIG. 1.

The slit mirror 14 acts as an optical amplifier, as it amplifies the scanning aperture of the beam 20. For example, with reference to FIG. 2, if the polygon 10 has 16 facets, it will rotate 22.5 degrees between facets and the resulting scanning aperture α of the beam 20 on the slit mirror 14 will be 45 degrees. After the beam 20 is scanned across the slit mirror 14, the scanning aperture β is 120 degrees.

Figure 3:
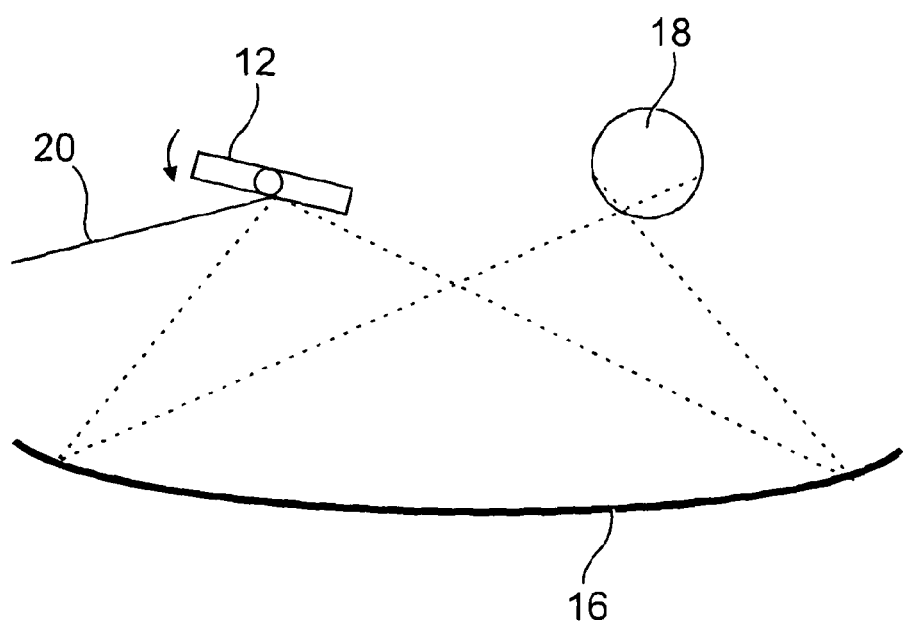
FIG. 3 is a second partial schematic view of the elements of FIG. 1.

With reference to FIG. 3, the beam 20 is then scanned across the main mirror 16 by the slow speed mirror 12 and reflected into the patient's eye 18. The source of collimated light 20a, the polygon 10 and the slow speed mirror 12 combine to provide a two-dimensional collimated light scan. The laser scanning system 1 therefore produces a scanned image comprising a number of lines of an object, e.g. a human retina.

The source of collimated light 20a, the polygon 10 and the slow speed mirror 12 may also combine to provide a two-dimensional collimated light scan from an apparent point source, and the apparent point source may be provided at the first focus point of the main mirror 16, such that the main mirror 16 transfers the two-dimensional collimated light scan from the apparent point source into the patient's eye 18.

The main mirror 16 may comprise an elliptical mirror, an aspherical mirror, an ellipsoidal mirror, a pair of parabola mirrors or a pair of paraboloidal mirrors.

The slit mirror 14 may comprise an elliptical mirror, an aspherical mirror, an ellipsoidal mirror, a pair of parabola mirrors or a pair of paraboloidal mirrors.

This type of laser scanning ophthalmoscope is described in the Applicant's European Patent Nos. 0730428 and 07733214.6.

FIG. 1 also illustrates a reference object 22. In the embodiment described and illustrated here the reference object 22 is a striped target comprising a series of alternate black and white bands. The bands are equally spaced with the width of each band being between approximately 0.25 mm and 0.75 mm. Ideally the width of each band is approximately 0.5 mm.

The reference object 22 is placed in the laser scanning system 1 before the system is used to obtain an image of the patient's retina.

The reference image is positioned between the polygon 10 and the slit mirror 14 such that is in the line of scan of the laser scanning system 1, i.e. the laser beam 20 moves across the reference object 22 during operation of the laser scanning system 1. The reference object 22 is therefore periodic in the direction of the line of scan of the laser scanning system 1.

With the reference object 22 positioned in the optical path after the polygon 10, i.e. between the polygon 10 and the slow speed mirror 12, the laser beam 20 repeatedly moves across the same portion of the reference object 22 to produce the reference image 24 (see FIG. 5 below). That is, the reference image 24 is constructed of a plurality of repeat image scans of the same portion of the reference object 22.

Figure 5:
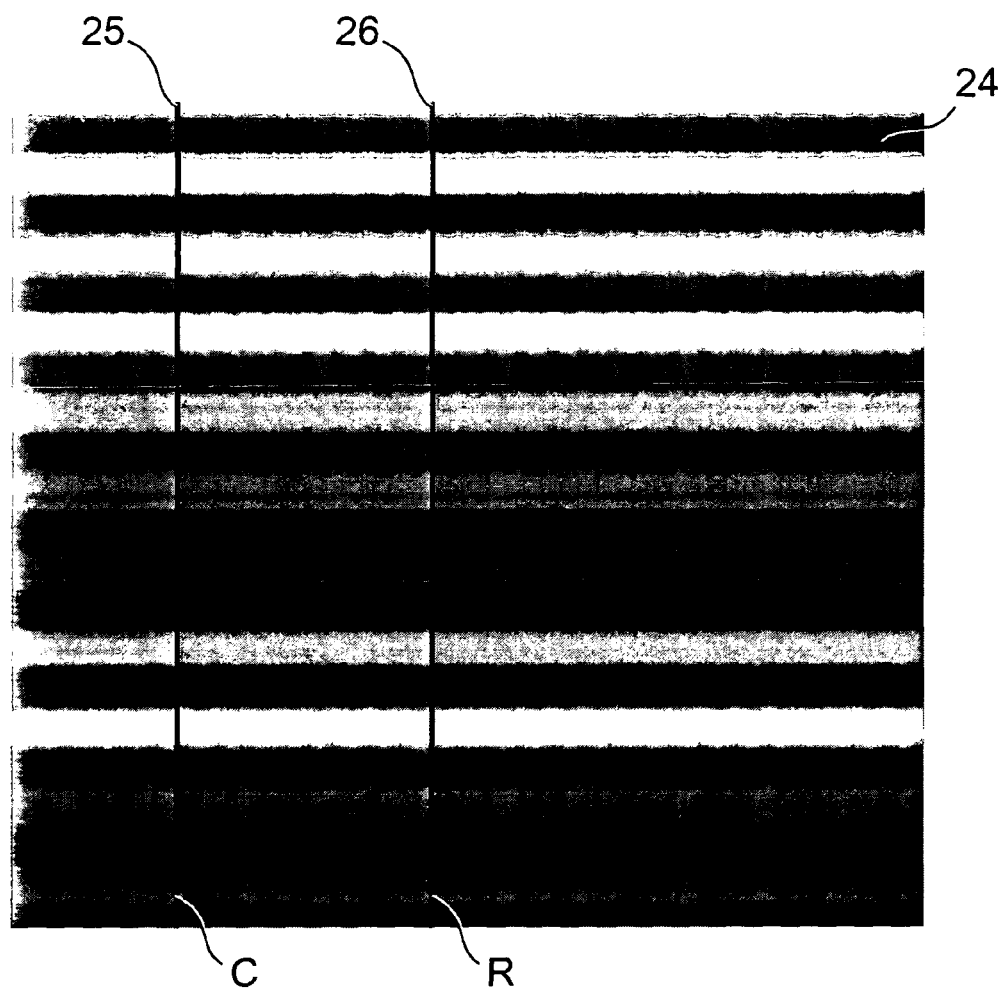
FIG. 5 is an example of a scanned image produced by the laser scanning system of FIG. 1.

As illustrated in FIG. 5, the reference image 24 comprises a plurality of columns 25 of alternate black and white bands. The reference image 24 may comprise a number of pixels.

Each column (scan line) 25 contains a jitter error that manifests itself as a vertical shift. That is, each column 25 of the reference image 24 contains a displacement along the scan direction of the polygon 10. This displacement is quasi-identical in columns occurring from the same polygon facet. That is, the displacement values are quasi-periodic. Small differences of less than ¼ pixel may result from noise in the system which prevents the displacements occurring from the same polygon facet from being exactly identical.

Typically, the reference image 24 comprises 3900 columns (and 3072 lines). However, it should be appreciated that the scanned reference image 24 may comprise any suitable number of columns 25.

The method for reducing the jitter error in the laser scanning system 1 will now be described with reference to FIGS. 4 to 8.

Figure 4:
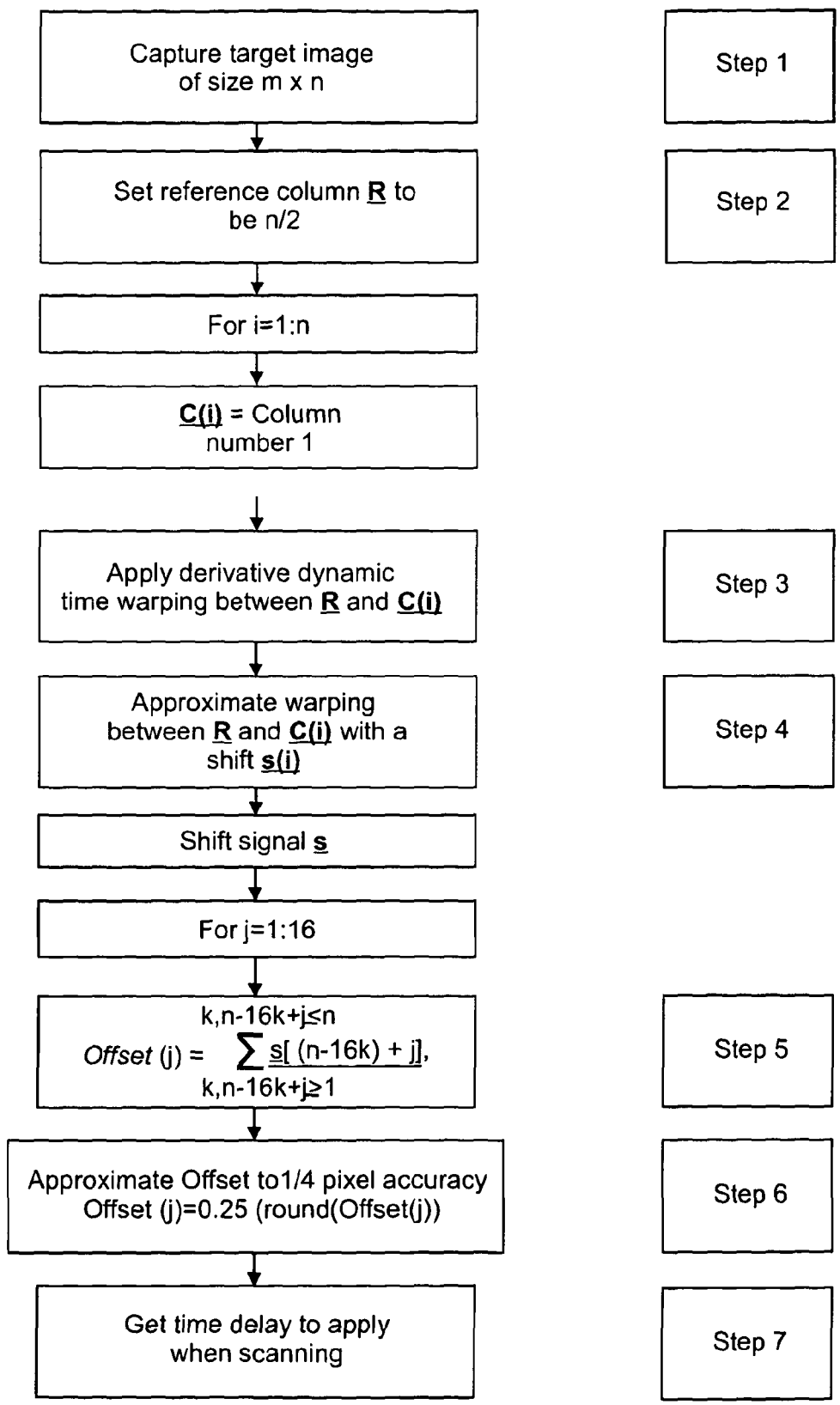
FIG. 4 is a flow chart detailing the method of reducing jitter error in the laser scanning system in accordance with the present invention.

With reference to FIG. 4, in step 1 the reference image 24 is captured by the laser scanning system 1. As described above, the laser beam 20 repeatedly moves across the striped target of the reference object 22 to produce the reference image 24 of FIG. 5. In obtaining the reference image 24 the laser scanning system 1 uses the green channel (i.e. wavelength of approximately 510 nm).

The reference image 24 may be a pixelated image with m rows of n columns (i.e. m×n). (For example, m=3072, n=3900).

Steps 2 to 6 describe how the reference image 24 is processed to calculate the error arising from non-repeatable displacement of the columns 25 of the reference image 24.

In step 2 a reference column 26 from the columns 25 of the reference image 24 is determined. The reference column 26 is determined using the formula n/2, where n is the total number of columns 25.

In step 3 the similarity between the reference column 26 and each of the other columns 25 is determined. The similarity between the reference column 26 and each of the other columns 25 is determined by using a dynamic time warping (DTW) algorithm or a derivative dynamic time warping (DDTW) algorithm. DTW and DDTW are known techniques for efficiently finding an alignment between two signals (or sequences). DDTW and DTW compare vectors locally, looking at local trends and/or variations between vectors.

In the embodiment described and illustrated here a DDTW algorithm is used to find alignment between the reference column signal and every other column signal. However, it should be appreciated that DTW may alternatively be used.

The warping between the reference column 26 and each of the other columns 25 is determined by firstly generating data signals (vector sequences) for each column 25 (including the reference column 26) which are representative of the image information of the column. The image information of the column may include the light intensity, or brightness, of the image and the data signals may include values which are representative of this intensity, or brightness. Where the reference image 24 is a pixelated image, the light intensity, or brightness, may include the light intensity or brightness of each pixel in the reference image.

The data signals may be represented as vectors:

$$R = r_1, r_2, \ldots, r_i, \ldots, r_n,$$

$$C = c_1, c_2, \ldots, c_j, \ldots, c_m,$$

where R is the reference column signal
C is one of the other column signals
n and m are the lengths of the signals.
(In the present embodiment m=n, as all columns have the same length=3072.)

Figure 6A:
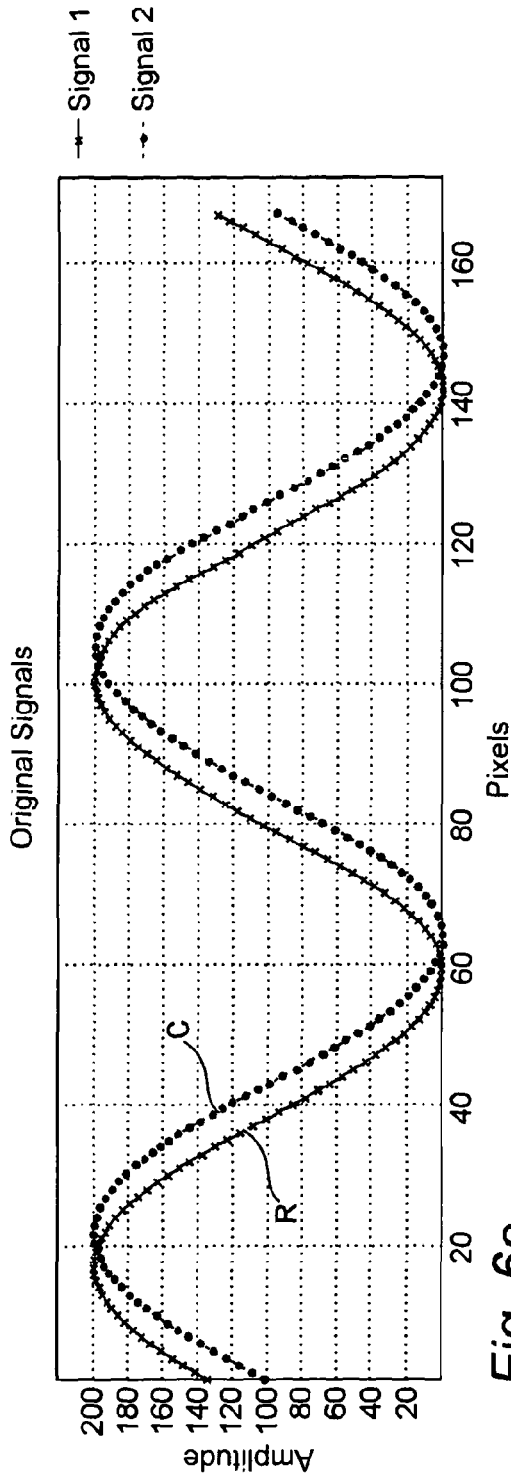
FIG. 6a is a graph illustrating two column data signals from the reference image of FIG. 5.

The data signals are illustrated in FIG. 6a. As illustrated in FIG. 6a, the two signals R and C are out of alignment with one another. As explained above, this is a result of the jitter error.

To find the alignment between the two signals using DDTW an n by m matrix is constructed where the $(i^{th}, j^{th})$ element of the matrix contains the pair-wise distance $d(r_i, c_j)$ between the two points $r_i$ and $c_j$. Using DDTW the distance $d(r_i, c_j)$ is not Euclidean but rather the square of the difference of the estimated derivatives of $r_i$ and $c_j$. The distance matrix is therefore:

$$D[i,j]((r_i)' - (c_j)')((r_i)' - (c_j)') \text{ with } 1 \leq i \leq m \text{ and } 1 \leq j \leq m,$$

where $(r_i)'$, $(r_j)'$, and $(c_j)'$ are the derivatives of $\underline{R}$ and $\underline{C}$ at points i and j.

Figure 7:
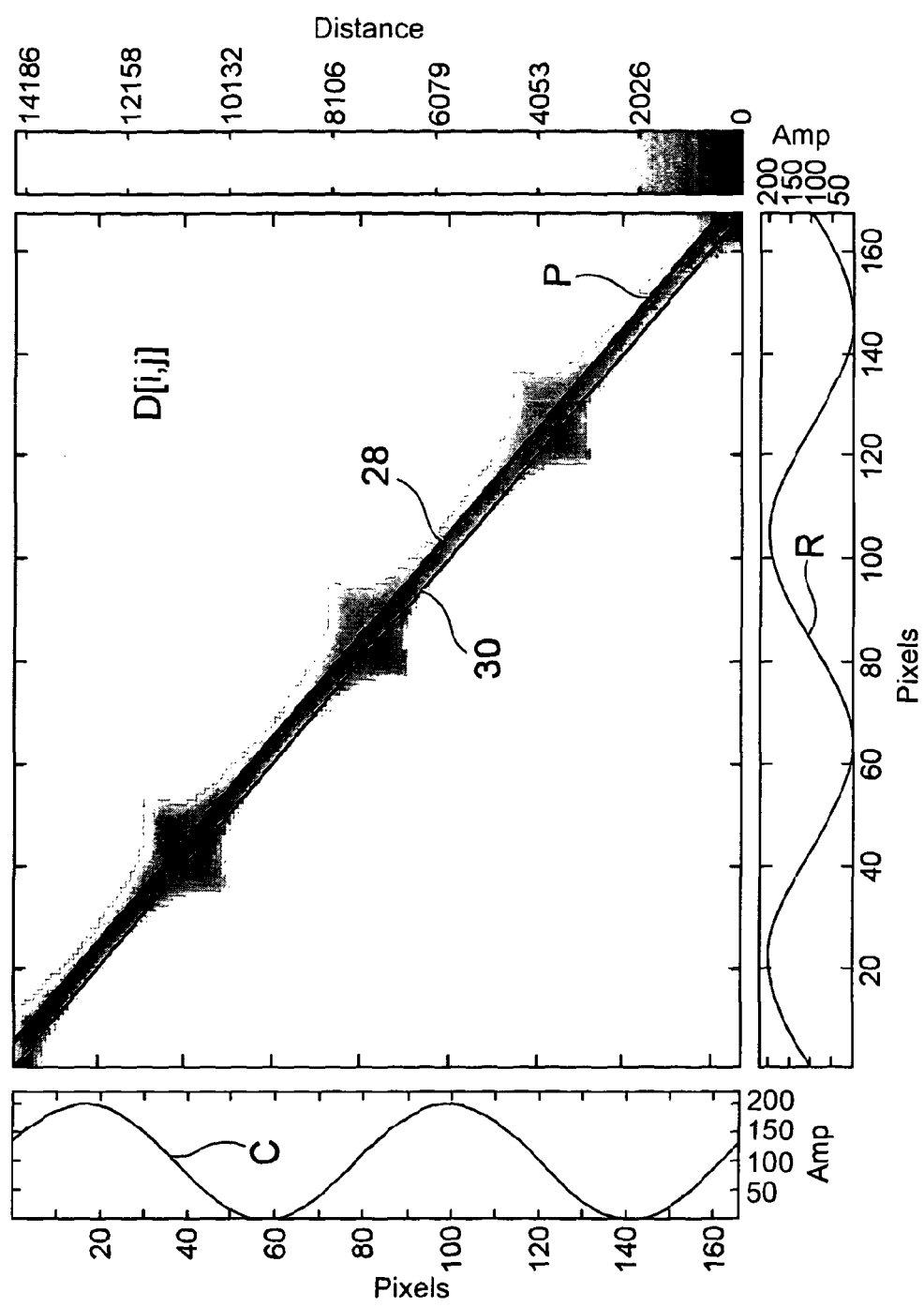
FIG. 7 is a pair-wise distance matrix between a reference column and a second column of the reference image.

Each matrix element (i,j) corresponds to the alignment between the points $r_i$ and $c_j$. The distance matrix $D[i,j]$ between the data signals $\ddot{R}$ and $\ddot{C}$ is illustrated in FIG. 7.

Once the matrix is constructed, the DDTW algorithm finds the alignment path which runs through the "low cost" areas, or "valleys", on the matrix. This alignment path is an example of a function representative of the minimal distance path of the matrix. The minimal distance path may be termed the "alignment path", the "optimal path", the "minimal cost path", the "warping path", or the "warping function".

The alignment path is a contiguous (in the sense stated below) set of matrix column and row indexes (or coordinates) that defines a mapping between $\underline{R}$ and $\underline{C}$.

The alignment path constructed by the DDTW algorithm may be expressed as:

$$P = (p_1, p_2, \ldots, p_k, \ldots, p_K) \text{ with } \max(m, n) \leq K < m + n - 1,$$

where the $k^{th}$ element of P is defined as $p_k = (px, py)_k$.

The alignment path P is subject to certain constraints:
(a) Boundary conditions: $p_1 = (1,1)$ and $p_K = (m,n)$. This requires the alignment path to start and finish in diagonally opposite corner cells of the matrix, i.e. the starting and end points of the alignment path must be the first and last points of the sequences.
(b) Monotonicity: Given $p_k = (a,b)$, then $p_{k-1} = (a',b')$ where $a - a' \geq 0$ and $b - b' \geq 0$. This forces the points in the alignment path P to be monotonically spaced in time, i.e. the coordinates of the alignment path must be increasing.
(c) Continuity: Given $p_k = (a,b)$, then $p_{k-1} = (a',b')$ where $a - a' \leq 1$ and $b - b' \leq 1$. This restricts the allowable steps in the alignment path P to adjacent cells (including diagonally adjacent cells), i.e. the path can only go one step up, or left, or both.

There may be many alignment paths which satisfy the above criteria. However, it is necessary to determine the path which minimizes the warping cost, i.e. the optimal path.

The optimal alignment path should minimize the warping cost:

$$DDTW(R, C) = \min\left(\frac{\sqrt{\sum_{k=1}^{K} p_k}}{K}\right),$$

where K in the denominator is used to compensate for the fact that the alignment paths may have different lengths.

The alignment path can be found by evaluating the following recurrence which defines the cumulative distance $\gamma(i,j)$ as the distance $d(i,j)$ found in the current cell and the minimum of the cumulative distances of the adjacent elements:

$$\gamma(i,j) = d(r_i, c_j) + \min\{\gamma(i-1,j), \gamma(i,j-1)\}.$$

The alignment path is illustrated in FIG. 7, referenced as 28. FIG. 7 also illustrates the reference column and other column data signals R and C.

The pseudo code for determining the matrix and the alignment path are detailed in Annexes 1 and 2.

Figure 6B:
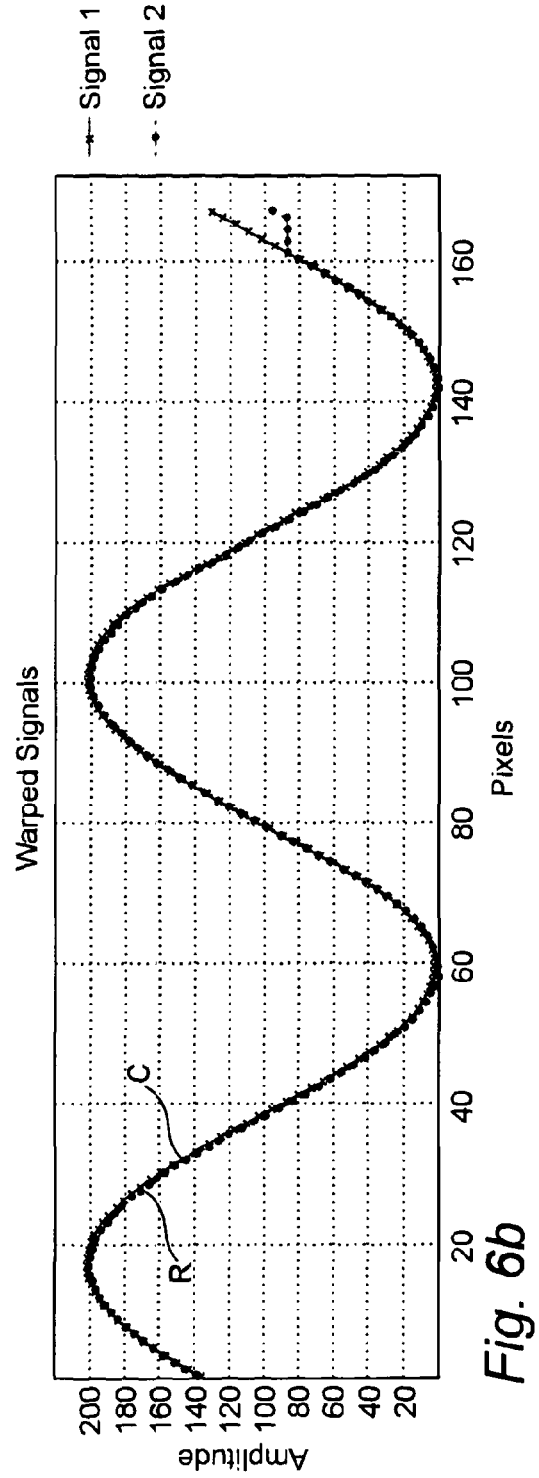
FIG. 6b is a graph illustrating the two column signals of FIG. 6a after an approximate shift has been applied to the second signal.

FIG. 6b illustrates the mapping of signal C onto signal R. As illustrated, once the alignment path is known it can be used to produce a close mapping of signals.

In step 4 the warping between the reference column data signals and the other column signals is approximated with a shift (or offset). The shift between signals corresponds to a column shift in the reference image 24. The column shift corresponds to the error arising from the non-repeatable displacement of the columns 25 of the reference image 24.

The alignment path has the form:

$$P=(p_1, p_2, \ldots, p_K)$$

with $p_k=(p_k x, p_k y)$ are the coordinates of each point in the path.

This is therefore the parametric representation of the curve of the alignment path.

The parametric representation is then transformed to an explicit form:

$$p_k y = f(p_k x) \text{ with } 1 \leq k \leq K.$$

The transformation is obtained by removing duplicates of the abscissas of p, obtaining their corresponding coordinates and then interpolating the results over the frame [1,m]. In the embodiment described here, m=n is the length of the two original signals R and C.

The pseudo code for removing the abscissas of p and interpolating the results over the frame [1,m] are detailed in Annexes 3 and 4.

The shift is obtained by comparing the implicit form of the alignment path with the diagonal reference path of the matrix.

The reference path of the matrix has a parametric representation X=t, Y=t, t in [1,N] where N is the signal length. The implicit form of the reference path is Y=X. The reference path would be the same as the alignment path if the two compared signals were identical. That is, the shift is obtained by comparing the discrete form of the alignment path with an "ideal path", i.e. the path that would exist if there were no warping between the two data signals.

The alignment path 28 and the reference path 30 are illustrated in FIG. 7.

The pseudo code for comparing the discrete form of the alignment path with the diagonal distance path of the matrix and obtaining the shift between each signal is detailed in Annex 5. The shift signal may be referenced as s (see FIG. 4).

It should be noted that the above-described shift is determined between the reference column 26 and every other column 25. The result of this is that n shift values for each column 25 (n=3900).

In step 5 the column shift for each facet of the polygon 10 is determined. Given that most of the jitter present in the reference image 24 is polygon facet dependent, the average of all the shifts of the columns 25 originating from the same polygon facet is averaged. In the case where the polygon 10 has 16 facets, these columns (or pixels) are separated by 16 columns (or pixels).

Figure 8:
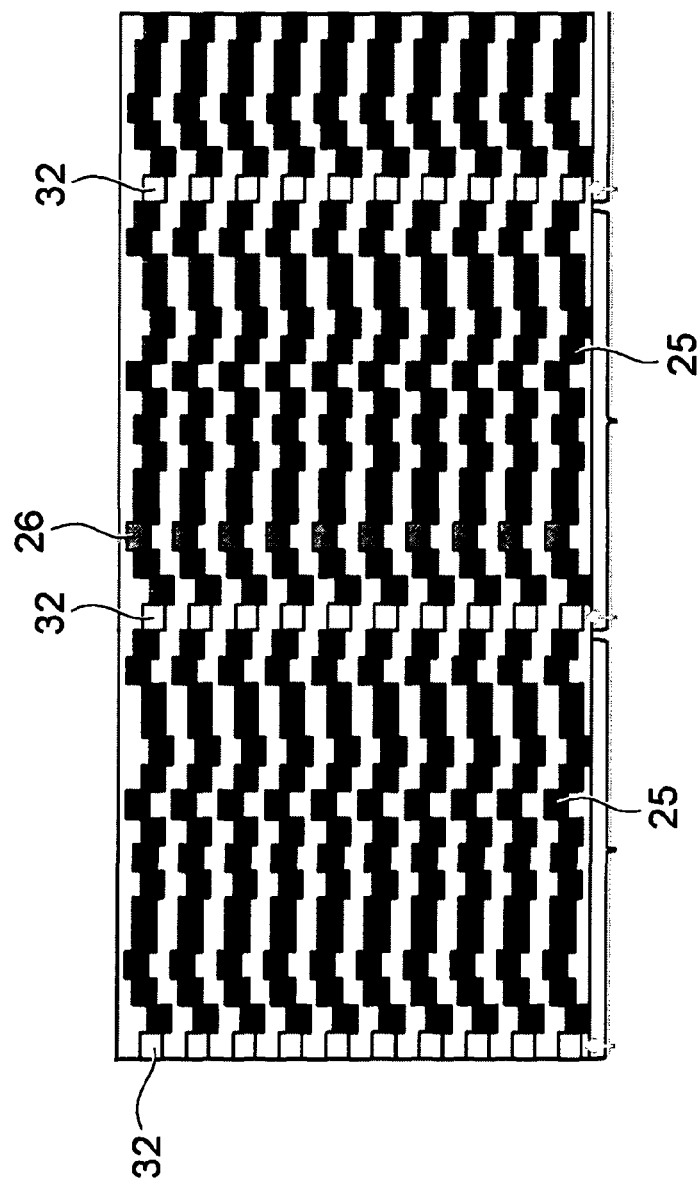
FIG. 8 is a schematic representation of the approximated column shift error in the reference image.

The column shift for each facet of the polygon 10 may be determined by:

$$\text{Offset}(j) = \sum_{k, n-16+j \geq 1}^{k, n-16k+j \leq n} s[(n-16k)+j],$$

where Offset(j) is the column shift for each facet and
  k k is an index representing image columns
  n number of columns in the image (n=3900)
  j variable corresponding to each facet. Here $1 \leq j \leq 16$ The approximated column shift error in the reference image 24 is illustrated in FIG. 8. Columns which originate from the same facet of the polygon 10 are referenced with the number 32. The reference column 26 is also illustrated.

FIG. 8 thus illustrates the averaged calculated error arising from non-repeatable displacement of the columns of the reference image 24. From FIG. 8 it can clearly be seen that the same column shift value has been assigned to each column 25 originating from the same facet of the polygon 10.

In step 6 the column shift (or offset) determined in step 5 is approximated to 0.25 pixel accuracy. This is due to the fact that the sampling of the scan has 0.25 pixel rate.

The approximated offset can be calculated by:

$$\text{Offset}(j)=0.25\times(\text{round}(\text{Offset}(j))).$$

Thus, for example, if the offset value was calculated as having a value of 1.6, it would be approximated to 0.25 pixel accuracy to 1.5.

In step 7 a scanning time delay (capture time) of the polygon 10 of the laser scanning system 1 is determined based on the approximated offset value determined in step 6. This scanning time delay of the polygon of the laser scanning system 1 is an example of an operating parameter of the laser scanning system 1.

In the embodiment described and illustrated here, each pixel of the reference image 24 is scanned at a frequency of 132 MHz, i.e. 7.57 ns.

This yields a linear relationship between the time delay and the offset of step 6 as:

$$\text{Time Delay(ns)}=7.57\times\text{Offset}(j).$$

This time delay is applied to each facet of the polygon 10 of the laser scanning system 1. That is, the time delay, or capture time, for each facet of the polygon is determined by advancing or delaying a reference capture time by a factor dependent upon the average approximate signal shift for that specific facet of the polygon.

The system may start imaging with the longest facet of the polygon 10. In order to know which shift corresponds to which facet of the polygon 10, the system 1 is forced to always start scanning using the longest facet. The facet data are recorded during an initial stage which imaging is started with facet 1, for example. The DDTW algorithm is run during this stage to obtain 16 shift values. s1 corresponding to facet 1, s2 corresponding to facet 2 etc. If a second image is captured, there is no way of knowing if the imaging will start with facet 1, and therefore no guarantee that the offsets will be applied correctly. To overcome this, imaging is started with the longest facet, as determined by the initial stage. Since the polygon always rotates in the same direction, and knowing the longest facet (or reference facet) and its offset, it is possible to attribute the remaining offsets correctly.

Figure 9:
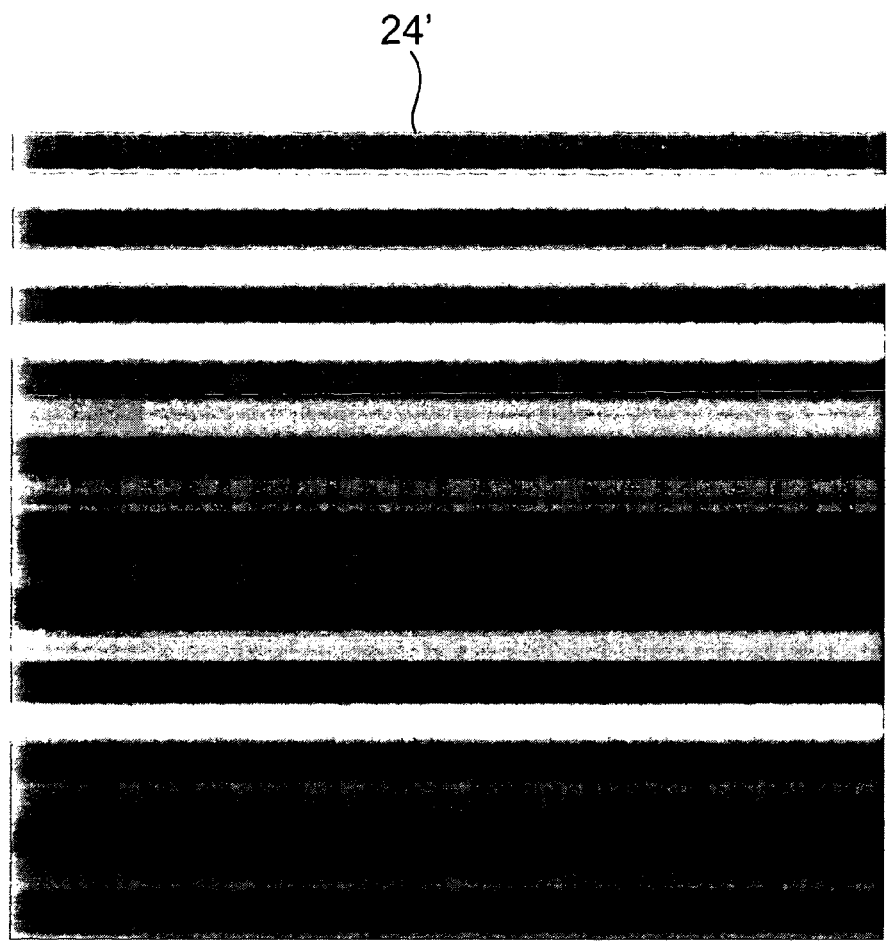
FIG. 9 is an example of a corrected scanned image produced by the laser scanning system of FIG. 1.

Once the time delay values (operating parameters) of the polygon 10 of the laser scanning system 1 have been adjusted in response to the calculated errors, the reference object 22 is scanned again. An example of the reduced jitter error reference object image 24' is illustrated in FIG. 9. It can clearly be seen that the jitter error has been reduced markedly from the original reference image 24 of FIG. 5.

Once the start of scan time delay/advance values of the polygon 10 of the laser scanning system 1 have been adjusted in response to the calculated errors, the reference object 22 is removed from the system and the system is used to obtain an image of the patient's retina in the normal manner. With this adjustment, the image of the patient's retina has a greatly reduced jitter error.

Steps 1 to 7 are preferably carried out by a computer, processing means, or the like. The steps 1 to 7 may be incorporated as part of the existing computer control software of the laser scanning system 1. The steps 1 to 7 may be provided on a separate computer, or the like, from the existing computer of the laser scanning system 1.

Step 7 is carried out by a computer, processing means, or the like, which is used to control the scanning elements 10, 12 of the laser scanning system 1. The software of the computer of the laser scanning system 1 controls the start of scan time 12. The software is reprogrammed to adjust the operating parameters of the laser scanning system 1 in response to the calculated error to correct for the non-repeatable displacement of the lines of the reference image 24.

Figure 10:
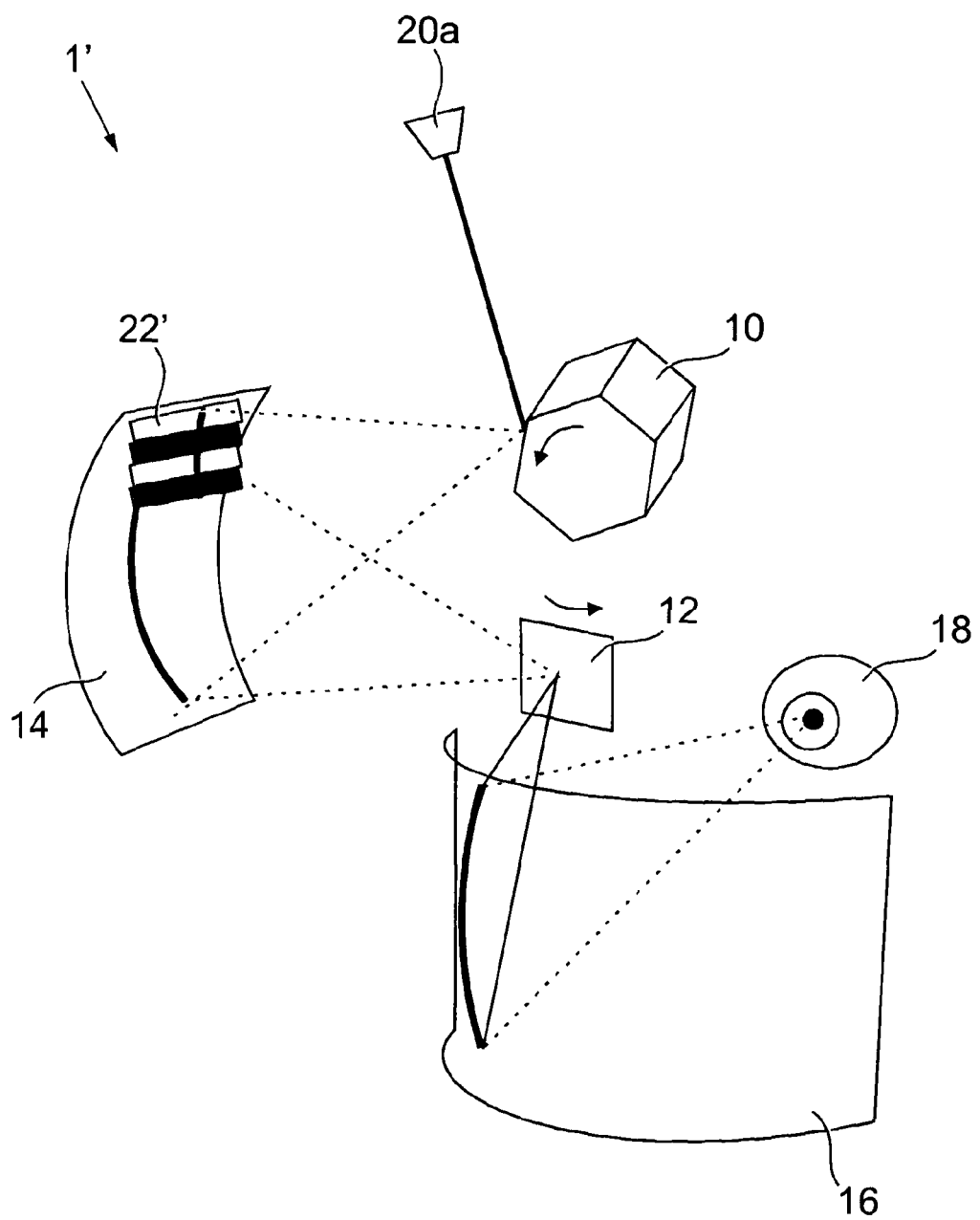
FIG. 10 is a schematic view of an alternative embodiment of the reflecting and scanning elements of the laser scanning ophthalmoscope of FIG. 1.

FIG. 10 is an alternative embodiment of the laser scanning system 1. The second embodiment is similar to the first embodiment, with the exception that the reference object 22' is located on the slit mirror 14.

The reference object 22' is placed on the edge of the slit mirror 14. Therefore, the scan laser beam 20 moves across the reference object 22' and the slit mirror 14 during operation of the laser scanning system 1'.

This means that the scanned image produced by the laser scanning system 1' includes an image of the patient's eye 18 and a reference image of the reference object 22'. That is, the scanned image is a two dimensional image which includes a portion of the patient's eye 18 and a portion of the reference object 22'.

In the embodiment described and illustrated here the reference object 22' covers approximately 2.5% of the scanning aperture and is imaged at the beginning of every scan line.

The method of reducing the jitter error in the laser scanning system 1' is the same as that described above in respect of the first embodiment of the laser scanning system 1.

The method of the present invention therefore obviates or mitigates the disadvantages of previous proposals by correcting for the jitter error introduced to the scanned image from the imperfect timing of the polygon facet position, the random noise introduced by the triggering system of the facet detector, the variations in the cut-depth of the facets of the polygon, the variations in the flatness of the facet of the polygon and the variations in the rotational speed of the polygon. The benefits of the method are increased jitter measurement accuracy, improved visual appearance of the scanned image, reduced facet detector accuracy requirements, reduced polygon building requirements, reduced polygon and facet detector failures in the field and improved polygon performance monitoring.

The method of the present invention exploits the linear dependency between imaging signal delay and pixel shifts and incorporates the shifts as timing delays when capturing the image. The method does not require any image processing, which reduces the computational cost. Since the method may be performed as a calibration before imaging of the patient's eye, the time taken to obtain the image of the patient's eye is unchanged, as the shift errors have already been corrected for beforehand.

Modifications and improvements can be made to the above without departing from the scope of the present invention. For example, although the laser scanning systems 1, 1' have been illustrated above as comprising slit mirrors 14, it is not essential that the system includes a slit mirror. In this case the reference object 22 is placed in the optical path after the polygon 10 or located on the main mirror 16.

Furthermore, it is also possible that the reference object 22 is positioned in the optical path after the slow speed mirror 12 and the polygon 10, i.e. the reference object 22 may be positioned in the system such that the polygon 10 and the slow speed mirror 12 combine to produce a two-dimensional raster scan light pattern across the reference object 22 to produce the reference image.

Also, the step of generating data signals for each column 25 may not necessarily include all columns in the reference image 24. It is possible to only generate data signals for a portion of these columns, i.e. a portion of the reference image.

Furthermore, although the method of reducing the jitter error in a laser scanning system has been described above with respect to the rotating polygon scanning element, it should be appreciated that the method could be applied to correcting for non-repeatable line displacement errors in the reference image caused by other scanning elements, e.g. oscillating plane mirrors (slow speed mirrors), or any other rotating and/or oscillating reflective elements used in the scanning system.

---

Annex 1

Accumulated Cost Matrix(X;Y;D)
//X and Y are input signals, D is the distance matrix defined as piece-
//wise squared distances between X and Y in the case of DTW, or //piece-
wise distances between the first derivatives of X and Y in the //case of
DDTW

---

```
1: m ←[X]    //m is the size of X
2: m ←[Y]    //m is the size of Y. In our case X and Y have the same length
3: ddtw[ ] ← new [m ,m] //allocate space for ddtw:the Accumulated Cost
Matrix
4: ddtw(0,0) ← 0         //initialize temporary variable
5: for i = 1; i ≤ m; i ++, do
6: ddtw(i; 1) ← ddtw(i−1; 1) + D(i; 1) //fill first column of ddtw
7: end for
8: for j = 1; j ≤ m; j ++, do
9: ddtw(1; j) ← ddtw(1; j−1) + D(1; j) //fill first column of ddtw
10: end for
11: for i = 1; i ≤ m; i ++, do
12: for j = 1; j ≤ m; j ++, do
13: ddtw(i; j) ← D(i; j)+min {ddtw(i − 1; j); ddtw(i; j − 1); ddtw(i − 1; j − 1)}//fill
```

-continued

---
Annex 1
---
rest of matrix
14: end for
15: end for
16: return ddtw //return accumulated cost matrix ddtw
---

---
Annex 2
---
Optimal Warping Path(ddtw)
---
```
 1: path[ ] ← new array //allocate space for the warping path
 2: i = rows(ddtw)    //i is an index for ddtw rows
 3: j = columns(ddtw) //j is index for ddtw columns
//The following steps fill the path by a backtracking algorithm from point
(m,m) to point (1,1)
 4: while (i > 1) & (j > 1) do
 5:   if i == 1 then
 6:      j = j − 1
 7:   else if j == 1 then
 8:      i = i − 1
 9:   else
10:         if ddtw(i−1; j) == min {ddtw(i − 1; j); ddtw(i; j − 1); ddtw(i − 1; j − 1)}
11:         then
12:            i = i − 1
13:         else if ddtw(i; j−1) == min {ddtw(i − 1; j); ddtw(i; j − 1); ddtw(i − 1; j − 1)}
14:            then
15:               j = j − 1
16:            else
17:               i = i − 1; j = j − 1
18:         end if
19:      path:add((i; j))
20:   end if
21: end while
22: return path
```
---

---
Annex 3
---
Remove Abscissa Duplicates(path)
//the path obtained from the Annex 2 is in the form (xk,yk) 1≤k≤K,
//we need to write this path in the form Yk=f(Xk) 1≤k≤K. To be able to do
so, we need remove duplicates from xk 1≤k≤K.
---
```
 1: new_path[ ] ← new array
 2: K = length(pathx) //K is the length of the x-coordinates (abscissas) of
the path
 3: new_pathx(1)=pathx(1)
 4: j=1    //initialize index of elements of newpath
 5: for i = 1; i ≤ K−1; i ++, do
 6:   if pathx(i+1)!=pathx(i)
 7:      new_pathx(j+1)=pathx(i+1)
 8:      new_pathy(j+1)=pathy(i+1)
 9:      j=j+1
10:   end if
11: end for
```
---

---
Annex 4
---
Interpolate New Path(x[1...m],xi[1..Ni], yi[1..Ni],))
//the previous step Annex3 gave a modified path without repetition.
// The new path doesn't necessarily cover all the range [1,m] where m is
the size of the input signals. We therefore interpolate the path to cover
each point in the range [1,m]. In this case x[1...m]=[1,2,3...m]
The output will be the y-coordinate corresponding to each element of
[1,2,3...m]
---

Annex 4

```
1: For i = 1; i ≤ m; i ++, do
2: if (x[i] ≤xi[1]) do
3: y[i] = yi[1];
4: end if
5: if (x[i] ≥xi[Ni]) do
6: y[i] = yi[Ni];
7: end if
8: j = 1;
9: while (j ≤m)
10: if (xi[j] >= x[i]) break;
11: j = j + 1;
12: end while
13: newPathInt[i] = yi[j−1] + (yi[j] − yi[j−1])*(x[i] − xi[j−1])/(xi[j]−xi[j−1]);
14: end for
```

Annex 5

```
Distance To Diagonal(new_pathInt)
//this algorithm approximates the warp with a shift.
//the shift is the distance between the path and the diagonal (defined as
y=x, or x=i, y=i 1≤i≤m)

1: Shift=0
2: for i = 1; i ≤ m; i ++, do
3: shift=shift+(new_path(i)−i)
4: end for
5: shift=shift/m
```

The invention claimed is:

1. A method of reducing jitter error in a laser scanning system adapted to produce a scanned image comprising a number of lines of an object, the method comprising the steps of:
providing a reference object arranged such that the scanned image produced by the laser scanning system includes a reference image of the reference object;
processing the reference image to calculate an error arising from non-repeatable displacement of the lines of the reference image; and
adjusting at least one operating parameter of the laser scanning system in response to the calculated error.

2. The method according to claim 1, wherein the reference object is periodic in a direction of a line of scan of the laser scanning system.

3. The method according to claim 1, wherein the reference object includes a series of alternate black and white bands.

4. The method according to claim 3, wherein the alternate black and white bands are equally spaced.

5. The method according to claim 4, wherein a width of each band is between 0.25 mm and 0.75 mm.

6. The method according to claim 1, wherein the reference image comprises a number of pixels.

7. The method according to claim 1, wherein the step of processing the reference image includes assigning one column of the reference image as a reference column.

8. The method according to claim 7, wherein the reference column is located around the center of the reference image.

9. The method according to claim 1, wherein the step of processing the reference image includes generating data signals for one or more columns which are representative of image information of the column.

10. The method according to claim 9, wherein the image information of the column includes light intensity, or brightness, of the image and the data signals include values which are representative of this intensity, or brightness.

11. The method according to claim 10, wherein the light intensity, or brightness, includes the light intensity or brightness of each pixel in the reference image.

12. The method according to claim 9, wherein data signals are generated for each column of the reference image.

13. The method according to claim 12, wherein the step of processing the reference image further includes comparing a given reference column data signal with one or more data signals from other columns.

14. The method according to claim 13, wherein the given reference column data signal is compared with every other column data signal.

15. The method according to claim 13, wherein the comparison between the given reference column data signal and the other column data signals further includes determining similarities between the signals.

16. The method according to claim 14, wherein the comparison between the given reference column data signal and the other column data signals includes determining warping between the signals.

17. The method according to claim 16, wherein the comparison between the given reference column data signal and the other column data signals includes using a dynamic time warping algorithm.

18. The method according to claim 17, wherein the comparison between the given reference column data signal and the other column data signals includes using a derivative dynamic time warping algorithm.

19. The method according to claim 13, wherein the comparison between the given reference column data signal and the other column data signal includes generating a matrix which is representative of pair-wise distances between the given reference column data signal and the other column data signal.

20. The method according to claim 19, wherein a matrix is generated for each comparison of the given reference column data signal with every other column data signal.

21. The method according to claim 19, wherein the distances between each column are defined in terms of pixels and the distance between corresponding points of each signal is represented by an integer number of pixels.

22. The method according to claim 13, wherein the comparison between the given reference column data signal and the other column data signal includes generating a matrix which is representative of pair-wise distances between the derivative of the given reference column data signal and the derivative of the other column data signal.

23. The method according to claim 22, wherein a matrix is generated for each comparison of the given reference column data signal with every other column data signal.

24. The method according to claim 22, wherein the derivative is the pair-wise distances between the first derivative of the given reference column data signal and the derivative of each of the other column data signals.

25. The method according to claim 23, wherein the comparison between the given reference column data signal and the other column data signals includes determining a function representative of a minimal distance path of the matrix.

26. The method according to claim 25, wherein the determination of the function representative of the minimal distance path of the matrix includes applying one or more constraints.

27. The method according to claim 26, wherein the constraints include that the function satisfies a boundary condition criteria, where starting and end points of the function must be the first and last points of the sequence.

28. The method according to claim 26, wherein the constraints further include that the function satisfies the monotonicity criteria.

29. The method according to claim 26, wherein the constraints further include that the function satisfies the continuity criteria.

30. The method according to claim 1, wherein the step of processing the reference image further includes determining an approximate signal shift between a given reference column data signal and each of other column data signals.

31. The method according to claim 30, wherein the signal shift corresponds to a column shift in the reference image.

32. The method according to claim 31, wherein the column shift corresponds to the error arising from quasi-periodic displacement of the columns of the reference image.

33. The method according to claim 30, wherein the determination of the approximate signal shift between the given reference column data signal and the other column data signals includes transforming a parametric representation of the function to an explicit form.

34. The method according to claim 33, wherein the transformation includes removing duplicates of the abscissas of the parametric curve.

35. The method according to claim 33, wherein the transformation includes interpolation of the explicit form of the function.

36. The method according to claim 35, wherein the determination of the approximate signal shift between the given reference column data signal and each of the other column data signals includes determining a distance between an interpolated path defined by the explicit form of the function and a reference path in a matrix.

37. The method according to claim 36, wherein the reference path in the matrix corresponds to the matrix diagonal.

38. The method according to claim 1, wherein the step of processing the reference image includes determining an average approximate signal shift for all column data signals originating from the same portion of a scanning element of the laser scanning system.

39. The method according to claim 1, wherein the step of processing the reference image includes determining an average approximate signal shift for all column data signals originating from the same facet of a rotating polygonal mirror.

40. The method according to claim 1, wherein the step of adjusting the at least one operating parameter of the laser scanning system in response to the calculated error may include adjusting a capture time of first or second scanning elements.

41. The method according to claim 40, wherein the capture time of the first or second scanning element is advanced and/or delayed.

42. The method according to claim 40, wherein, when the first or second scanning element is a rotating polygonal mirror, each facet of the polygon has a specific capture time.

43. The method according to claim 42, wherein the capture time for each facet of the polygon is determined by advancing or delaying a reference capture time by a factor dependent upon the average approximate signal shift for that specific portion of the scanning element.

44. The method according to claim 1, wherein the laser scanning system further comprises a source of collimated light.

45. The method according to claim 1, wherein the laser scanning system further comprises first and second scanning elements.

46. The method according to claim 45, wherein the first scanning element is a rotating polygonal mirror and the second scanning element is an oscillating plane mirror.

47. The method according to claim 45, wherein the reference object is positioned in an optical path of the laser scanning system after the first scanning element.

48. The method according to claim 45, wherein a source of collimated light and the first and second scanning elements combine to provide a two-dimensional collimated light scan.

49. The method according to claim 45, wherein the second scanning element is positioned in an optical path of the laser scanning system after the first scanning element and the reference object is positioned after the second scanning element.

50. The method according to claim 1, wherein the laser scanning system further comprises scan transfer means having two foci.

51. The method according to claim 50, wherein a source of collimated light and first and second scanning elements combine to provide a two-dimensional collimated light scan from an apparent point source, and an apparent point source is provided at a first focus of the scan transfer means and an object is accommodated at a second focus of the scan transfer means, and wherein the scan transfer means transfers the two-dimensional collimated light scan from the apparent point source to the object.

52. The method according to claim 51, wherein the object is an eye and the scan transfer means transfers the two-dimensional collimated light scan from the apparent point source into the eye.

53. The method according to claim 50, wherein the scan transfer means comprises on of the group consisting of an elliptical mirror, an asphehcal mirror, an ellipsoidal mirror, a pair of parabola mirrors or a pair of paraboloidal mirrors.

54. The method according to claim 1, wherein the laser scanning system further comprises scan relay means.

55. The method according to claim 54, wherein a source of collimated light, first and second scanning elements, and the scan relay means combine to provide a two-dimensional collimated light scan from an apparent point source.

56. The method according to claim 54, wherein the scan relay means comprises two foci.

57. The method according to claim 56, wherein one foci of the scan relay means is coincident with one foci of a scan transfer means.

58. The method according to claim 54, wherein the scan relay means comprises at least one of of an elliptical mirror, an asphehcal mirror, an ellipsoidal mirror, a pair of parabola mirrors, and a pair of paraboloidal mirrors.

59. The method according to claim 54, wherein the reference object is located on one of scan transfer means or the scan relay means.

60. The method according to claim 1, wherein the scanned image produced by the laser scanning system includes an image of the object and the reference image of the reference object.

61. The method according to claim 60, wherein the image of the object and the reference image of the reference object occur beside one another on the scanned image.

\* \* \* \* \*